United States Patent
Chen et al.

(10) Patent No.: US 11,693,919 B2
(45) Date of Patent: Jul. 4, 2023

(54) ANATOMY-AWARE MOTION ESTIMATION

(71) Applicant: SHANGHAI UNITED IMAGING INTELLIGENCE CO., LTD., Shanghai (CN)

(72) Inventors: Xiao Chen, Lexington, MA (US); Pingjun Chen, Gainesville, FL (US); Zhang Chen, Brookline, MA (US); Terrence Chen, Lexington, MA (US); Shanhui Sun, Lexington, MA (US)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 326 days.

(21) Appl. No.: 16/908,148

(22) Filed: Jun. 22, 2020

(65) Prior Publication Data

US 2021/0397886 A1    Dec. 23, 2021

(51) Int. Cl.
| | | |
|---|---|---|
| *G06F 18/213* | (2023.01) | |
| *G16H 50/50* | (2018.01) | |
| *G16H 30/20* | (2018.01) | |
| *G16H 50/70* | (2018.01) | |
| *G16H 50/20* | (2018.01) | |
| *G16H 30/40* | (2018.01) | |
| *G06V 40/20* | (2022.01) | |
| *G06N 3/08* | (2023.01) | |
| *G06F 18/214* | (2023.01) | |

(52) U.S. Cl.
CPC ........ *G06F 18/213* (2023.01); *G06F 18/2148* (2023.01); *G06N 3/08* (2013.01); *G06V 40/20* (2022.01); *G16H 30/20* (2018.01); *G16H 30/40* (2018.01); *G16H 50/20* (2018.01); *G16H 50/50* (2018.01); *G16H 50/70* (2018.01); *G06V 2201/031* (2022.01)

(58) Field of Classification Search
None
See application file for complete search history.

(56) References Cited

U.S. PATENT DOCUMENTS

| | | | |
|---|---|---|---|
| 2005/0013501 A1* | 1/2005 | Kang | G06T 5/50 382/254 |
| 2009/0028403 A1* | 1/2009 | Bar-Aviv | G06V 10/754 382/128 |
| 2013/0121577 A1* | 5/2013 | Wang | G06T 7/20 382/173 |
| 2015/0170400 A1* | 6/2015 | Seitz | H04N 13/207 345/427 |

(Continued)

FOREIGN PATENT DOCUMENTS

WO    WO-2021144230 A1 *    7/2021

*Primary Examiner* — Delomia L Gilliard
(74) *Attorney, Agent, or Firm* — Zhong Law, LLC (57) ABSTRACT

Described herein are neural network-based systems, methods and instrumentalities associated with estimating the motion of an anatomical structure. The motion estimation may be performed utilizing pre-learned knowledge of the anatomy of the anatomical structure. The anatomical knowledge may be learned via a variational autoencoder, which may then be used to optimize the parameters of a motion estimation neural network system such that, when performing motion estimation for the anatomical structure, the motion estimation neural network system may produce results that conform with the underlying anatomy of anatomical structure.

20 Claims, 5 Drawing Sheets

(56) References Cited

U.S. PATENT DOCUMENTS

| | | | |
|---|---|---|---|
| 2017/0337682 A1* | 11/2017 | Liao | G06T 7/0012 |
| 2018/0218502 A1* | 8/2018 | Golden | G06N 3/08 |
| 2018/0225822 A1* | 8/2018 | Zhou | G06T 7/0012 |
| 2019/0134425 A1* | 5/2019 | van Baar | A61N 5/1077 |
| 2020/0167928 A1* | 5/2020 | Heindl | G06N 3/08 |
| 2020/0327674 A1* | 10/2020 | Yang | G06T 7/143 |
| 2021/0216878 A1* | 7/2021 | Norman | G06T 7/33 |
| 2021/0233645 A1* | 7/2021 | Morard | G06T 7/38 |
| 2021/0264589 A1* | 8/2021 | Jacob | G06T 7/143 |

* cited by examiner

ANATOMY-AWARE MOTION ESTIMATION

BACKGROUND

Motion estimation plays an important role in many medical applications. For example, cardiac motion estimation can be used to calculate subject-specific muscular strain of the myocardium, which could be beneficial for the treatment of cardiac arrhythmia, ischemia, cardiomyopathy, valve diseases, etc. The time-varying motion of an anatomical structure such as the heart can be estimated using deep learning techniques, for example, by analyzing the visual features of multiple images of the structure recorded at different points in time (e.g., as in a video) and tracking the changes occurring between the images. Conventional deep learning-based motion estimation techniques rely heavily on image content (e.g., image intensities) without considering the anatomy of the target structure. Those techniques also require significant amounts of segmentation work or annotation efforts. As a result, the accuracy of conventional motion estimation is often affected by tissues or organs around a target structure that have similar image appearances as the target structure, or by the difficulty in obtaining ground truth data for a motion.

Accordingly, it is desirable to improve the conventional motion estimation techniques to ensure the accuracy of the estimation results and reduce the reliance on annotated training data. For example, it may be desirable to train a motion estimation system to acquire knowledge about the anatomy of a target anatomical structure in addition to its visual features and utilize the knowledge to reduce anatomically un-realistic motion estimation. Further, to circumvent the difficulty in obtaining ground truth for motion estimation, it may also be desirable to constrain the output of the motion estimation system and/or to optimize its parameters based on one or more alternative sources of information such that the training of the motion estimation system may be conducted in a minimally supervised manner with a limited amount of annotated training data.

SUMMARY

Described herein are neural network-based systems, methods and instrumentalities associated with motion estimation. A motion estimation neural network system (e.g., which may be referred herein as a motion tracker) as described herein may be trained to receive a first medical image that comprises a first visual representation of an anatomical structure and a second medical image that comprises a second visual representation of the anatomical structure. The motion estimation neural network system may be further trained to extract a first plurality of features from the first medical image and a second plurality of features from the second medical image, determine a first motion of the anatomical structure based on the first and second pluralities of features, and generate a first flow field indicating the first motion. The first motion may be determined by treating the first medical image as a source image and the second medical image as a target image and determining a displacement of the anatomical structure from the first medical image to the second medical image.

The motion estimation neural network system may be trained at least partially using a variational autoencoder (VAE) to perform the aforementioned tasks. The VAE may be pre-trained to learn a shape prior of the anatomical structure and, during the training of the motion estimation neural network system, the VAE may be used to constrain at least one output of the neural network system based on the shape prior of the anatomical structure. For example, the VAE may be pre-trained using a training dataset that represents a shape distribution of the anatomical structure and, through the pre-training, the VAE may learn to receive an input segmentation mask associated with the anatomical structure and generate a corrected version of the input segmentation mask that conforms with the shape distribution of the anatomical structure. Then, during the training of the motion estimation neural network system, the neural network system may estimate a baseline flow field based on two input training images of the anatomical structure and generate a warped segmentation mask for the anatomical structure based on the baseline flow field. The motion estimation neural network system may further obtain, from the VAE, a reference segmentation mask for the anatomical structure that corresponds to the warped segmentation mask. As described herein, such a reference segmentation mask may be generated by the VAE in accordance with the shape prior of the anatomical structure. Based on the reference segmentation mask, the motion estimation neural network system may adjust one or more of its operating parameters with an objective to reduce the difference between the warped segmentation mask and the reference segmentation mask.

By training the motion estimation neural network system with the anatomy-aware VAE described herein, shape or anatomy prior may be infused into the motion estimation neural network system such that, at an inference time, the motion estimation neural network system may predict an anatomically correct motion of the anatomical structure, for example, without having to perform additional anatomy or shape correction operations during processing or post-processing (e.g., the VAE may be used only during the training of the motion estimation neural network system and not at the inference time).

In examples, the difference between the warped segmentation mask and the reference segmentation mask may be determined based on respective latent space variables associated with the warped segmentation mask and the reference segmentation mask. In examples, the difference between the warped segmentation mask and the reference segmentation mask may be determined based on an estimated flow field between the warped segmentation mask and the reference segmentation mask.

The motion estimation neural network system may have a symmetrical structure and may, in addition to determining the first motion and the first flow field, determine a second motion of the anatomical structure based on the first and second pluralities of features and generate a second flow field indicating the second motion. The second motion may be determined, for example, by treating the second medical image as the source image and the first medical image as the target image and determining a disparity of the anatomical structure from the second medical image to the first medical image. In addition, the motion estimation neural network system may also generate first and second warped images based on the first and second flow fields and the first and second medical images, respectively. The motion estimation neural network system may further refine the first or second warped image by estimating a third flow field that indicates a third motion of the anatomical structure from one of the first or second warped image to the second or first input medical image, and generate a third warped image based on the third flow field and one of the first or second warped image. The first and second medical images described herein may be neighboring image frames comprised in a magnetic resonance imaging (MRI) video and the training of the motion estimation neural network system may be conducted in a minimally supervised manner (e.g., with only a first image frame being annotated and the rest of the image frames being tracked by the motion tracker or corrected by the VAE).

BRIEF DESCRIPTION OF THE DRAWINGS

A more detailed understanding of the examples disclosed herein may be obtained from the following description, given by way of example in conjunction with the accompanying drawing.

DETAILED DESCRIPTION

The present disclosure is illustrated by way of example, and not by way of limitation, in the figures of the accompanying drawings.

Figure 1:
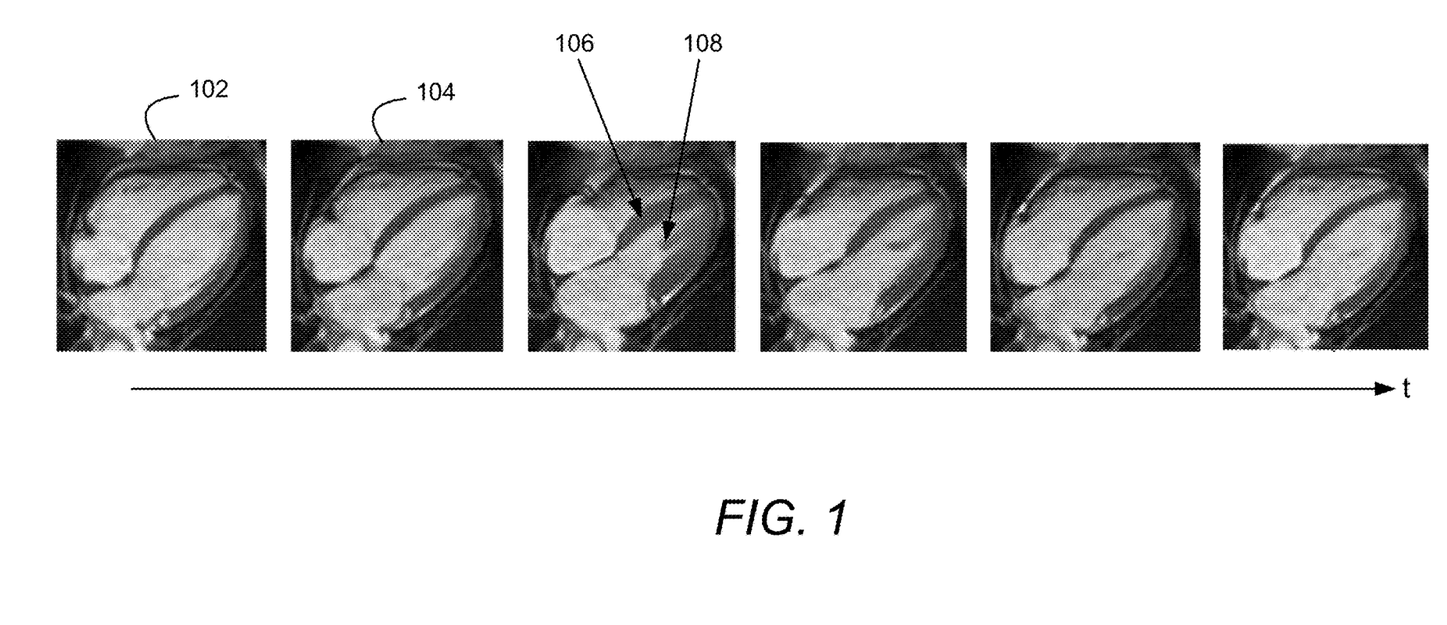
FIG. 1 is a simplified block diagram illustrating an example of cardiac motion estimation using myocardial feature tracking (FT) techniques.

FIG. 1 is a block diagram illustrating an example of estimating time-varying cardiac motion using myocardial feature tracking (FT) techniques. The motion estimation may be performed based on a magnetic resonance imaging (MRI) video of the heart such as a cine MRI that comprises a plurality of images of the heart recorded at different points in time (e.g., sequential points in time along a time axis t). The cine MRI may depict one or more complete cycles of cardiac contraction and relaxation. For example, the image frames in FIG. 1 show the heart motion starting from relaxation to contraction and then back to relaxation. As such, starting from a first image frame 102 of the cine MRI, the motion of the heart (e.g., the myocardium) between the first image frame 102 and a second image frame 104 may be estimated by comparing the two image frames and identifying changes that have occurred between the time the first image frame 102 is recorded and the time the second image frame 104 is recorded. The second image frame 104 may then be used as a new reference frame, and the estimation process may be repeated for the remaining frames to obtain motion information for a full cardiac cycle.

Various techniques may be used to estimate the motion of the myocardium between two images. In examples, a motion estimation system may first segment the images to identify the myocardium in the images and then apply feature tracking to the segmentation results (e.g., binary segmentation masks) to determine the myocardial differences in the two images. The training of such a motion estimation system may require a substantial amount of annotated data. And since image features inside and/or outside the myocardium may be discarded during the segmentation (e.g., before feature tracking is applied), the accuracy of the motion estimation may be affected.

In other examples, an image content-based motion estimation system may determine the motion of the myocardium directly from the images using deep learning-based models and methods. Such a system may face the challenge of having insufficient ground truth data for the myocardial motion and as such may be trained in an unsupervised manner. In addition, since portions of the myocardium (e.g., the left ventricular muscle 106) may have similar appearance in the cine MRI images as one or more neighboring issues or organs (e.g., the papillary muscles 108), the image content-based motion estimation system may need to resolve the ambiguity in those muscle areas in order to prevent anatomically unrealistic estimation results.

A motion estimation system may be trained to consider the anatomy (e.g., shape) of a target structure when tracking motion of the target structure. The training may be performed in a weakly supervised (e.g., minimally supervised) manner by utilizing pre-learned shape prior of the target structure to constrain or refine the output of the motion estimation system. One or more examples are provided herein to illustrate the configuration, training, and operation of such an anatomy-aware motion estimation system. The examples are described in the context of cardiac motion estimation, but those skilled in the art will appreciate that the disclosed systems, methods and instrumentalities may also be used to estimate the motion of other anatomical structures and/or in other application areas.

Figure 2:
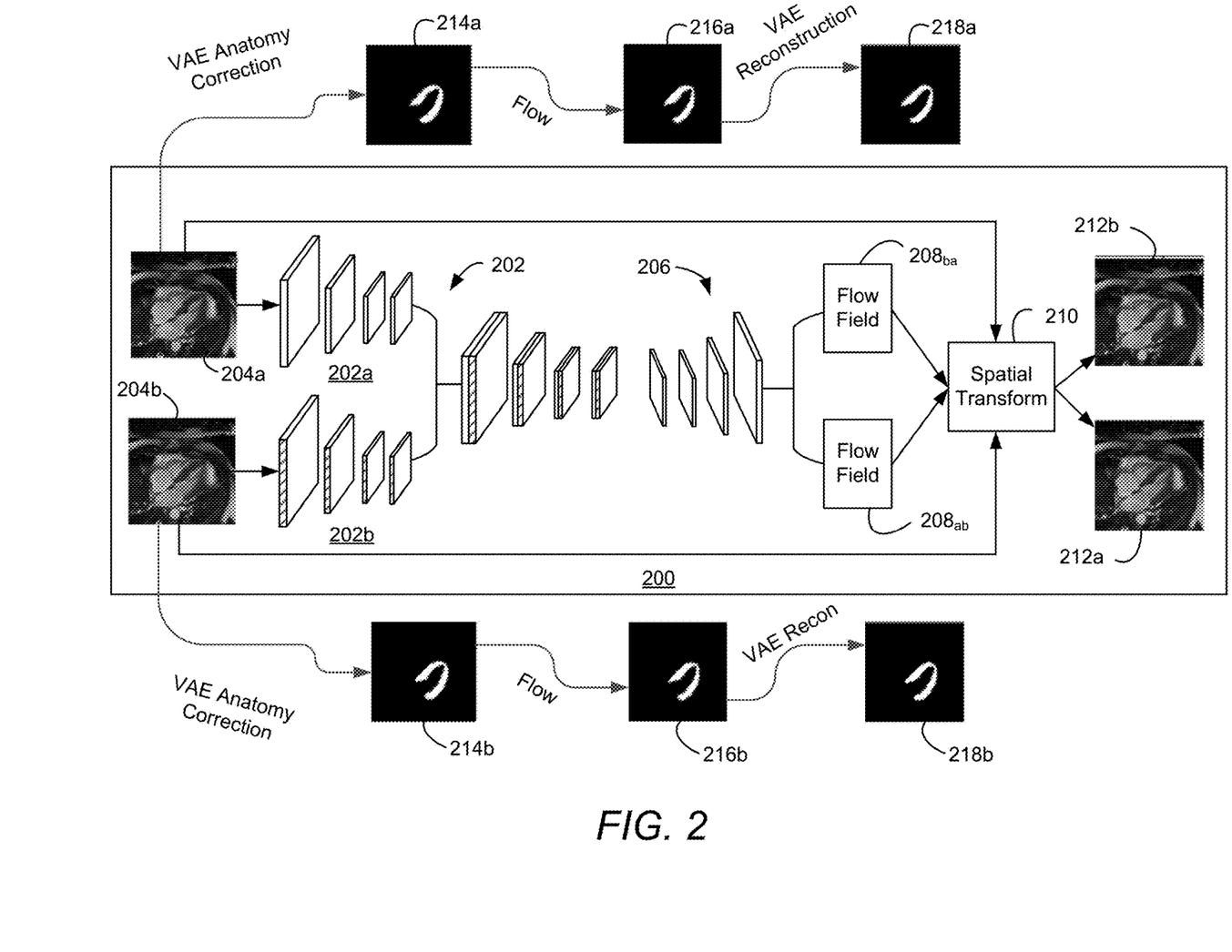
FIG. 2 is a simplified block diagram illustrating an example motion estimation neural network system and the training of the neural network system.

FIG. 2 is a block diagram illustrating an example motion estimation neural network system 200 and the training of the neural network system. The motion estimation neural network system 200 may comprise a feature tracking neural network 202 configured to receive a pair of input images 204a and 204b and extract features from the images. In examples, the feature tracking networking 202 may comprise twin subnetworks 202a and 202b arranged in a Siamese configuration to process the respective input images 204a and 204b in tandem (e.g., the subnetworks 202a and 202b may be twin neural networks having the same operating parameters or weights). Each of the subnetwork 202a and 202b may comprise one or more artificial neural networks such as one or more convolutional neural networks (CNNs) or fully convolutional neural networks (FCNs). Each of these artificial neural networks may comprises a plurality of layers such as one or more convolutional layers, one or more pooling layers, and/or one or more fully connected layers. Each of the convolutional layers may include a plurality of convolution kernels or filters configured to extract specific features from the input images 204a and 204b. The convolution operation may be followed by batch normalization and/or non-linear activation, and the features extracted by the convolutional layers e.g., in the form of one or more feature maps) may be down-sampled through the pooling layers and/or the fully connected layers (e.g., using a 2×2 window and a stride of 2) to reduce the redundancy and/or dimension of the features (e.g., by a factor of 2).

As a result of the series of down-sampling and/or convolution operations through the layers of the neural networks, respective representations (e.g., latent space representations) of the features of the input images 204a and 204b may be obtained, for example, in the form of twin feature maps or feature vectors, and at multiple levels of scale and abstraction. The respective feature maps or vectors of the input images 204a and 204b may be compared or matched, for example, at a patch level (e.g., patch by patch), and/or via a correlation layer.

The motion estimation neural network system 200 may further comprise a flow estimation network 206 (e.g., a multi-scale decoder network) configured to infer a flow between the input images 204a and 204b based on the features of the images. The inference may be performed, for example, based on matches (or displacement) between the features of the input images, which, as described herein, may be indicated by the similarity metric or score map produced by the feature extraction network 202.

The flow estimation network 206 may comprise one or more neural networks such as one or more CNNs or FCNs each having a plurality of layers. Through these neural network layers, the flow estimation network 206 may perform a series of up-sampling and transposed convolution (e.g., deconvolution) operations on the feature maps or feature vectors produced by the feature extraction network 202 (e.g., at multiple levels of scale and abstraction) to obtain a flow field (e.g., an up-sampled flow field) that indicates the disparity or displacement between the input images 204a and 204b. For example, the flow field may include a vector field, a grid of vectors, a vector-value function, and/or the like that indicates the disparity or displacement between the input images, and as such, the flow field may be used to estimate the motion of a target anatomical structure between the input images. As shown in FIG. 2, the flow estimation network 206 may comprise one or more un-pooling layers and one or more convolutional layers. Using the un-pooling layers, the flow estimation network 206 may up-sample the feature representations produced by the feature extraction network 202, e.g., based on pooled indices stored by the feature extraction network. The flow estimation network 206 may then process the up-sampled representations through the convolutional layers, for example, via one or more transposed convolution or deconvolution operations (e.g., using 3×3 transposed convolutional kernels with a stride of 2) and/or one or more batch normalization operations to derive one or more dense feature maps (e.g., which may be up-scaled by a factor of 2). Based on the feature maps, the flow estimation network 206 may predict a flow field $208_{ab}$ (e.g., a high resolution flow field) that represents the displacement of features from the input image 204a to the input image 204b.

The motion estimation neural network system 200 may further comprise a spatial transformation network 210 (e.g., a differentiable spatial transformation network) configured to generate a warped image 212a based on the input image 204a and the flow field $208_{ab}$. For example, the spatial transformation network 210 may include an input layer, one or more hidden layers (e.g., convolutional layers), and/or an output layer. In operation, the spatial transformation network 210 may take the input image 204a (e.g., a feature map of the input image 204a generated by the feature extraction network 202) and/or the flow field 208ab as input, obtain a plurality of transformation parameters, for example, based on the flow field 208ab (e.g., based on the displacement indicated by, the flow field $208_{ab}$), and use the transformation parameters to create a sampling grid that includes a set of points where the input image 204a is to be sampled to produce the transformed or warped image 212a. The input image and the sampling grid may then be provided to a sampler of the transformation network 210 to produce an output image (e.g., the warped image 212a) sampled from the input image 204a at the grid points.

As shown in FIG. 2, the motion estimation neural network system 200 may be symmetric in the sense that it may not only include the twin subnetworks 202a and 202b for extracting respective features from the input images 204a and 204b, it may also be configured to perform one or more of the operations described herein to generate a second flow field $208_{ba}$ that represents the displacement of features from the input image 204b to the input image 204b and a second warped image 212b created based on the input image 204b and the flow field $208_{ba}$. For example, in a first set of operations, the motion estimation neural network system 200 may treat the input image 204a as a source image and the input image 204b as a target image, and generate the flow field 208ab and the warped image 212a via the feature extraction network 202, the flow estimation network 206 and the spatial transformation network 210. In a second set of operations, the motion estimation neural network system 200 may treat the input image 204b as the source image and the input image 204a as the target image, and generate the flow field $208_{ba}$ and the warped image 212b via the feature extraction network 202, the flow estimation network 206 and the spatial transformation network 210.

The symmetric structure of the motion estimation neural network system 200 may bring several benefits. For example, by processing the pair of input images through two iterations, data augmentation may be achieved. Further, using the symmetric framework, additional keypoints may be obtained from both input images to steer the estimation of disparity between the two images. As a result, the accuracy of the estimation may be improved.

The feature extraction network 202, flow estimation network 206 and spatial transformation network 210 may learn their respective parameters (e.g., weights) through individualized as well as end-to-end training. In examples, the training may involve learning a shape prior of a target anatomical structure (e.g., the myocardium) and using the pre-learned shape prior to constrain the output of one or more of the networks so that motion of the target anatomical structure may be estimated in conformance with the underlying anatomy of the target anatomical structure.

FIG. 2 further illustrates how the motion estimation neural network system 200 may be trained to become anatomy-aware. In a first stage of the training process, the motion estimation neural network system 200 may be configured to make a baseline motion estimation for a pair of input images ($\mathcal{I}_1$, $\mathcal{I}_2$) (e.g., such as the input images 204a and 204b). The input images ($\mathcal{I}_1$, $\mathcal{I}_2$) may be from a cardiac cine MRI and the first stage of the training may be performed in an unsupervised manner. Using initial operation parameters (e.g., weights) that may be sampled from one or more probability distributions or obtained from another neural network with a similar architecture, the motion estimation neural network 200 may extract respective features from the pair of input images and predict flow fields $\vec{F}_{12}$ and $\vec{F}_{21}$ (e.g., the flow field $208_{ab}$ and $208_{ba}$) that indicate the displacement between the two input images ($\mathcal{I}_1$, $\mathcal{I}_2$). For example, the flow field $\vec{F}_{12}$ may represent the displacement between the images when $\mathcal{I}_1$ is treated as the source image and $\mathcal{I}_2$ is treated as the target image. Conversely, the flow field $\vec{F}_{21}$ may represent the displacement between the images when $\mathcal{I}_2$ is treated as the source image and $\mathcal{I}_1$ is treated as the target image. Based on the features of the input images ($\mathcal{I}_1$, $\mathcal{I}_2$) and the predicted flow fields $\vec{F}_{12}$ and $\vec{F}_{21}$, the motion estimation neural network system 200 may generate, via the spatial transformation network 210, respective warped images ($\mathcal{I}'_1$, $\mathcal{I}'_2$) (e.g., the warped images 212a and 212b) corresponding to the input image ($\mathcal{I}_1$, $\mathcal{I}_2$) and the flow fields $\vec{F}_{12}$ and $\vec{F}_{21}$.

Denoting $\otimes$ as a warping operator applied by the spatial transformation network 210, the warped image $\mathcal{I}'_1$ may be expressed as $\mathcal{I}'_1 = \mathcal{F}_{12} \otimes \mathcal{I}_1$ and the warped image $\mathcal{I}'_2$ may be expressed as $\mathcal{I}'_2 = \mathcal{F}_{21} \otimes \mathcal{I}_2$. A loss function for optimizing the parameters of the motion estimation neural network system 200 (e.g., to enforce warping consistency) may be defined as $L_{cons} = (\|\mathcal{I}_1 - \mathcal{I}'_2\| + \|\mathcal{I}_2 - \mathcal{I}'_1\|)$. Further, in at least some examples, a Huber loss $L_H = \mathcal{R}(\mathcal{F}_{12}) + \mathcal{R}(\mathcal{F}_{21})$ may be included as a motion smoothness regularizer for the flow fields, and the loss function for the baseline estimation may be expressed as $$L_{base} = L_{cons} + \lambda_H L_H, \qquad (1)$$

where $\lambda_H$ may represent the Huber loss weight (e.g., $\lambda_H$ may be set to 0.02 during the training of the baseline model).

The baseline parameters of the motion estimation neural network system 200 derived during the first stage of the training may be refined or optimized, for example, in a second stage of the training process in which an anatomy-aware neural network may be introduced to enforce an anatomy constraint (e.g., a shape constraint) on the output and/or parameters of the motion estimation neural network system 200. Example embodiments will be described herein using a variational autoencoder (VAE) as an example of the anatomy-aware neural network. It should be noted, however, that the disclosed systems, methods, and instrumentalities are not restricted to using a VAE and may instead use other types of neural networks to acquire knowledge about the anatomy (e.g., a shape prior) of a target structure and apply the knowledge to the training of the motion estimation neural network system 200.

The anatomy-aware neural network utilized in the second stage of the training may include a convolutional VAE pre-trained (e.g., before being used to constrain the motion estimation neural network system 200) to learn the anatomy of the target structure (e.g., the myocardium) being estimated by the motion estimation neural network system 200. For example, the VAE may be trained on sample images of the myocardium that represent a prior shape distribution of the myocardium to become capable of receiving a segmentation mask of the myocardium and generating a reconstructed version of the segmentation mask that corrects unrealistic representations of the myocardium in accordance with the anatomy (e.g., shape) of the myocardium. The training of the VAE will be described in greater detail below.

FIG. 2 illustrates how the pre-trained VAE may be used to optimize the parameters of the motion estimation neural network system 200. As shown, during the second stage of the training process, a coarse segmentation mask for the myocardium as depicted by the input image 204a may be obtained via the baseline estimation (e.g., during the first stage of the training process) and the coarse segmentation mask may be corrected by the pre-trained VAE to derive a VAE-corrected segmentation mask 214a for the myocardium. Since the VAE has been pre-trained to learn the anatomy of the myocardium, the VAE-corrected segmentation mask 214a may be in conformance with the anatomy (e.g., the shape prior) of the myocardium and as such may be used as the ground truth of the segmentation mask corresponding the input image 204a. In a similar manner; a coarse segmentation mask for the myocardium as depicted by the input image 204b may be obtained via the baseline estimation (e.g., during the first stage of the training process) and the coarse segmentation mask may be corrected by the pre-trained VAE to derive a VAE-corrected segmentation mask 214b for the myocardium that may serve as the ground truth of the segmentation mask corresponding to the input image 204b.

Based on these VAE-corrected segmentation masks 214a and 214b, warped segmentation masks 216a and 216b may be derived using baseline estimation of the flow fields $208_{ab}$ and $208ba$; respectively. Respective losses (e.g., representing anatomy related losses) between the warped segmentation mask 216a and the VAE-corrected segmentation mask 214b, and between the warped segmentation mask 216b and the VAE-corrected segmentation mask 214a, may then be determined and used to refine the flow fields $208_{ab}$ and flow fields $208ba$ (e.g., by optimizing the parameters of the feature extraction network 202 and/or the flow estimation network 206) to minimize the losses. For example, denoting the VAE-corrected segmentation mask 214a as $M_1$ and the warped segmentation mask 216a as $M'_1$, $M'_1$ may be represented by $M'_1 = \mathcal{F}_{12} \otimes M_1$. Similarly, denoting the VAE-corrected segmentation mask 214b as $M_2$ and the warped segmentation mask 216b as $M'_2$, $M'_2$ may be represented by $M'_2 = \mathcal{F}_{12} \otimes M_2$. An anatomy loss function $L^M_{anat}$ may then be expressed as $L^M_{anat} = |M_1 - M'_2| + |M_2 - M'_1|$ and used to optimize the parameters of the motion estimation neural network system 200.

In examples, the VAE model described herein may also be applied to the warped segmentation masks 216a and 216b to obtain VAE-reconstructed segmentation masks 218a and 218b, respectively. The VAE-reconstructed segmentation masks may be used to further refine the flow fields 208ab and flow fields 208ba, e.g., by forcing the warped segmentation masks 216a and 216b to respectively approximate (e.g., to be close to) the VAE-reconstructed segmentation masks 218a and 218b. For instance, respective losses (e.g., representing reconstruction related losses) between the warped segmentation mask 216a and the VAE-reconstructed segmentation mask 218a, and between the warped segmentation mask 216b and the VAE-reconstructed segmentation mask 218b, may be determined and used to optimize the parameters of the feature extraction network 202 and/or the flow estimation network 206 to minimize the reconstruction losses. Denoting the VAE-reconstructed segmentation mask 218a as $M_1^{recon}$ and the VAE-reconstructed segmentation mask 218b as $M_2^{recon}$, a reconstruction loss function may be defined as $L^M_{recon} = |M'_1 - M_1^{recon}| + |M'_2 - M_2^{recon}|$. Combining the anatomy loss function $L^M_{anat}$, the reconstruction loss function $L^M_{recon}$ and the loss function for the baseline estimation, a loss function for the shape-constrained motion estimation described herein may be as follows:

$$L = L_{cons} + \lambda_H L_H + \lambda_{anat} L^M_{anat} + \lambda_{recon} L^M_{recon} \qquad 2)$$

where $\lambda_H$, $\lambda_{anat}$, and $\lambda_{recon}$ may represent the respective weights associated with the Huber loss, the anatomy loss and the reconstruction loss as described herein. In examples, the values of $\lambda_H$, $\lambda_{anat}$, and $\lambda_{recon}$ may set to 0.04, 6.0 and 1.2, respectively.

Figure 3:
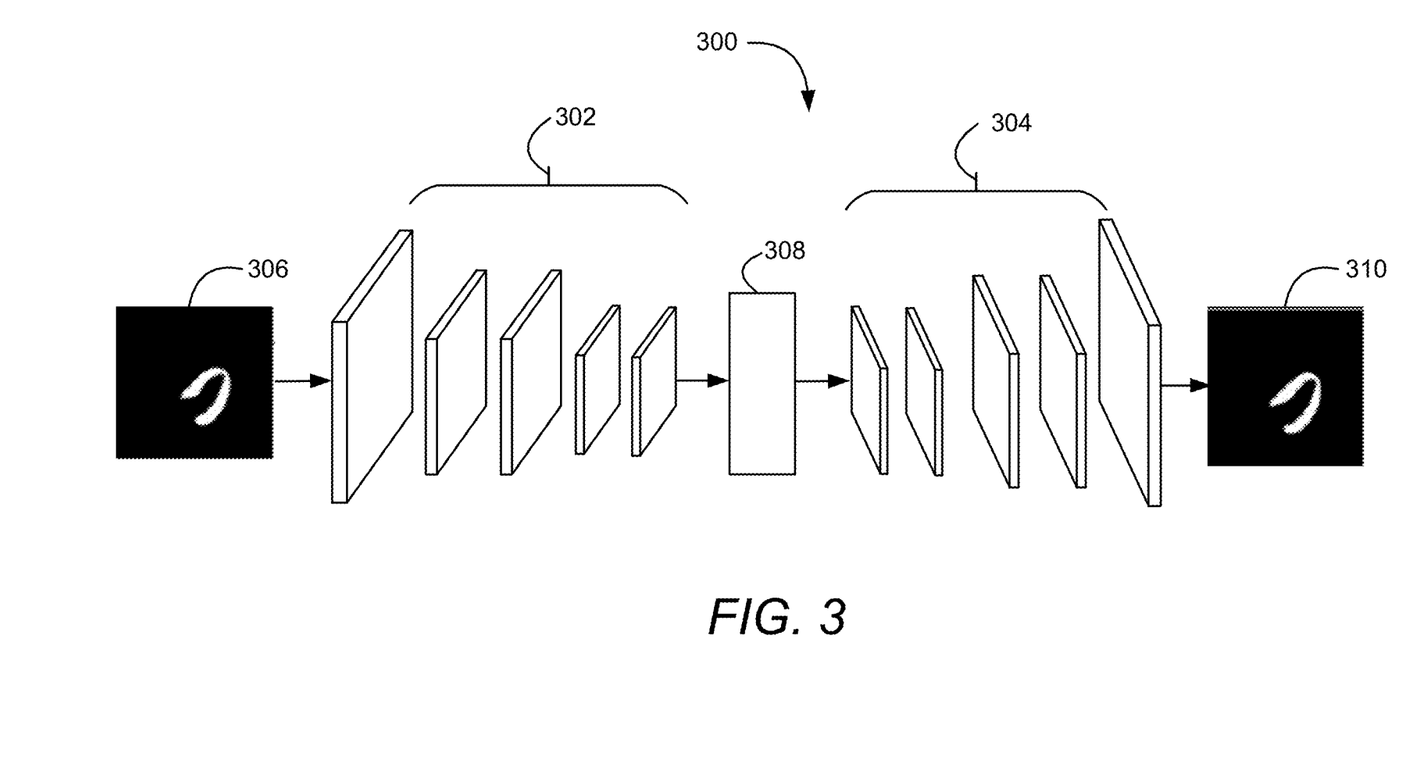
FIG. 3 is a simplified block diagram illustrating an example neural network that may be used to facilitate the training of the motion estimation neural network system described herein.

FIG. 3 is a block diagram illustrating an example neural network 300 (e.g., the VAE described herein) that may be trained to facilitate the training of the motion estimation neural network system 200. As shown, the neural network 300 may comprise an encoder network 302 and a decoder network 304. The encoder network 302 may be configured to receive a segmentation mask 306 as an input and produce a latent space representation 308 of the features of the segmentation mask (e.g., a low-resolution or low-dimension representation) as an output. The encoder network 302 may be a convolutional neural network or a fully convolutional neural network and may comprise a plurality of layers including one or more convolutional layers and/or one or more pooling layers. The encoder network 302 may be trained to produce the representation 308 by performing a series of down-sampling and/or convolution operations on the input mask 306 through the layers of the neural network. Each of the convolutional layers of the encoder network 302 may include a plurality of convolution kernels or filters configured to extract specific features from the input mask 306. The convolution operation may be followed by batch normalization and/or non-linear activation, and the features extracted by the convolutional layers (e.g., in the form of one or more feature maps) may be down-sampled through the pooling layers (e.g., using a 2×2 window and a stride of 2) to reduce the redundancy and/or dimension of the features (e.g., by a factor of 2). The latent space representation 308 resulting from the down-sampling and convolutional operations may be in various forms including, for example, a latent variable or vector Z that represents a mapping between the input mask 306 and a posterior distribution. For instance, the latent variable Z may include a fix-sized vector and each element of the vector may correspond to a respective probabilistic score for an image category or classification.

The decoder network 304 may be configured to receive the representation 308 generated by the encoder 302 and reconstruct the input mask 306 based on the representation 308 to obtain a reconstructed mask 310 that contains pixel- or voxel-level details of the image content. The decoder network 308 may be a convolutional neural network or a fully convolutional neural network comprising a plurality of layers (e.g., un-pooling and/or convolutional layers). Through these layers, the decoder network may perform a series of up-sampling and/or transposed convolution (e.g., deconvolution) operations to interpret the representation 308 produced by the encoder network 302 and recover spatial details of the input mask 306. For instance, the decoder network 304 may up-sample the representation 308 via the un-pooling layers, e.g., based on pooled indices stored by the encoder 302. The decoder network 304 may then process the up-sampled representation through the convolutional layers (e.g., using 3×3 transposed convolutional kernels with a stride of 2) to produce a plurality of dense feature maps (e.g., up-scaled by a factor of 2) before applying batch normalization to the feature maps to obtain the reconstructed segmentation mask 310 (e.g., a high dimensional or high resolution mask). In examples, the reconstructed segmentation mask 310 may correspond to a multi-class, pixel/voxel-wise probabilistic maps in which pixels or voxels belonging to each of the multiple classes are assigned a high probability value to indicate the classification of the pixels/voxels.

The neural network 300 may be trained using annotated sample images of the target object (e.g., the myocardium) to be estimated by the motion estimation neural network system 200. The sample images may represent a shape distribution of the target object (e.g., the sample images may represent different shape variations of the target object in the general population) and as such the neural network 300 may learn the shape prior of the target object by processing the sample images through the encoder network 3002 and the decoder network 304. In addition to a reconstruction loss, the training of the neural network 300 may also utilize a distribution loss such as a Kullback-Leibler Divergence (KLD) loss to enforce the latent space representation 308 to conform to a standard normal distribution. As a result, the output of the encoder network 302 may include a mean vector and a standard deviation vector, and the decoder network 304 may reconstruct the mask 310 by sampling from the standard normal distribution based on the mean and standard deviations.

The trained neural network 300 (e.g., including the encoder network 302 and the decoder network 304) may be used to correct anatomically unrealistic myocardium masks. For example, given an input mask, a mean latent variable representing an expected myocardium manifold in the latent space may be used without sampling, and the decoder 304 may decode such a latent variable into a realistic shape, for example, to mitigate disturbances presented in the input mask. Further, to improve the robustness of the neural network 300, training data may be augmented, for example, by flipping the training images in the vertical and/or horizontal directions, by rotating the images by 90, 180, or 270 degrees followed by a random rotation in the range of −45 to ±45 degrees, and/or by setting the latent space as a 32-dimensional representation.

Figure 4:
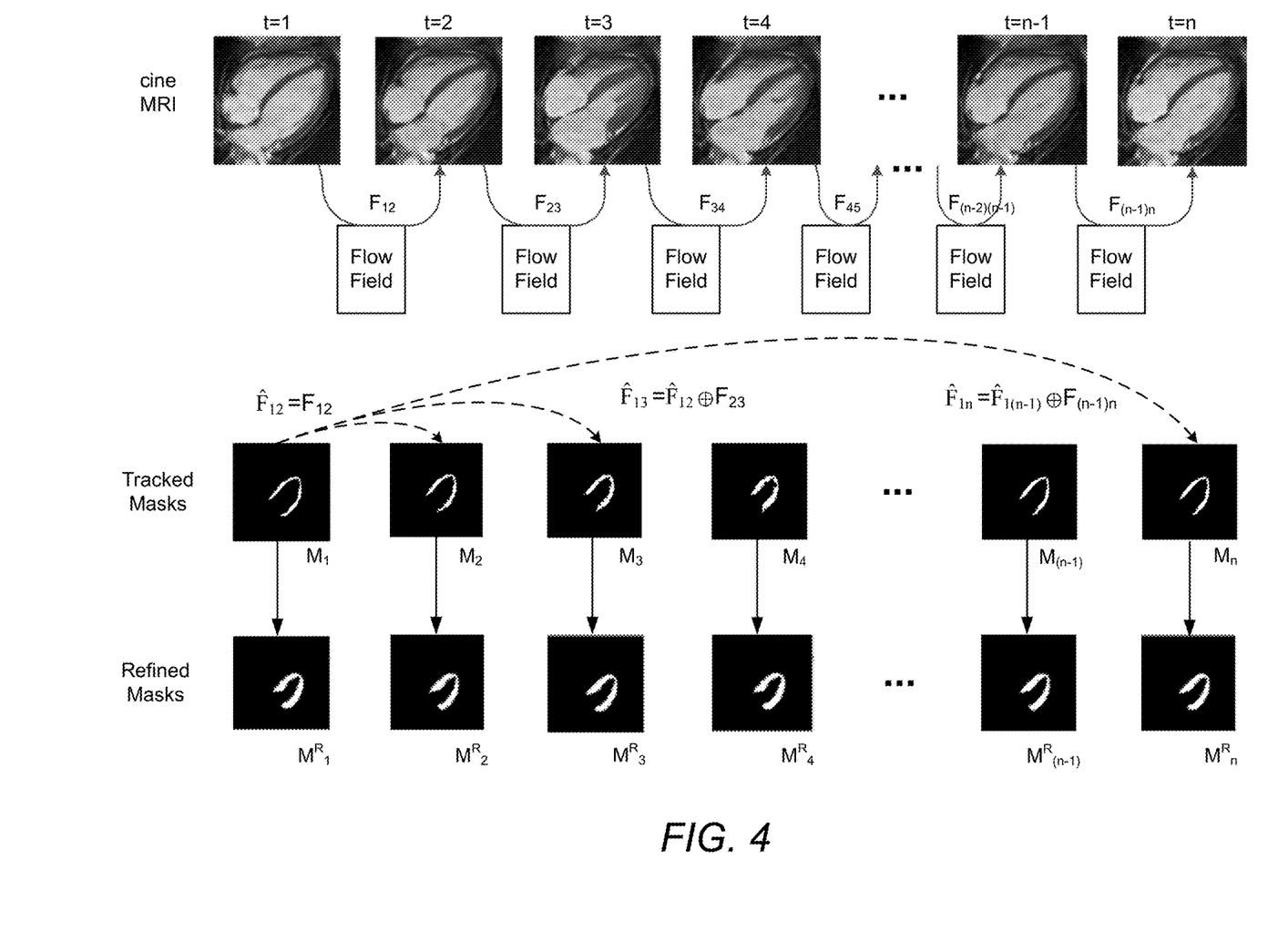
FIG. 4 is a simplified block diagram illustrating motion estimation based on a cardiac cine MRI.

FIG. 4 is a block diagram illustrating how a motion estimation neural network system (e.g., the motion estimation neural network system 200) may be trained to perform feature tracking and/or motion estimation for a cine MRI (e.g. a cardiac cine MRI). As shown, the cine MRI may comprise a plurality of image frames recorded at different points in time (e.g., represented by t=1, t=2, . . . t=n−1 and t=n). In a first stage of the operation, the motion estimation neural network system may make a baseline prediction of one or more flow fields, $F_{12}$, $F_{23}$, $F_{34}$, . . . $F_{(n-2)(n-1)}$ and $F_{(n-1)n}$, each of which may represent a respective displacement of features between a respective pair image frames (e.g., a pair of neighboring frames). Based on these predicted flow fields, the motion estimation neural network system may estimate the cardiac motion represented by the cine MRI by computing a composite flow field between an end-diastolic (ED) image frame and the n-th image frame. Without loss of generality, it is assumed herein that the first image frame of the cine MRI is the ED frame and as such, a composite flow field $\hat{F}_{1n}$ may be determined as follows:

$$\hat{F}_{1n} = \begin{cases} F_{12}, & n = 2 \\ \hat{F}_{1(n-1)} \oplus F_{(n-1)n}, & n > 2 \end{cases} \quad 3)$$

where $\oplus$ represents a flow composite operator and $F_{ij} \oplus F_{jk} = F_{ij} \otimes F_{ij} + F_{ij}$, with i and j having values between 1 and n, and $\otimes$ representing a warping operator.

In the example shown in FIG. 4, the motion estimation neural network system may track the myocardium in the cine MRI during the baseline estimation to predict respective coarse segmentations (e.g., $M_1$, $M_2$, $M_3$, $M_4$ . . . $M_{(n-1)}$, and $M_n$) of the myocardium in one or more of the cine MRI image frames. The coarse segmentations of the myocardium may be corrected by a pre-trained anatomy-aware neural network (e.g., such as the anatomy-aware VAE described herein) to obtain respective corrected segmentations $M^R_1$, $M^R_2$, $M^R_3$, $M^R_4$, . . . $M^R_{(n-1)}$ and $M^R_n$ of the myocardium corresponding to the coarse segmentations $M_1$, $M_2$, $M_3$, $M_4$, . . . $M_{(n-1)}$ and $M_n$. The parameters of the motion estimation neural network system may then be adjusted based on the loss function defined in Equation 2) such that, at an inference time, the motion estimation neural network system may directly estimate the cardiac motion (e.g., omitting one or more post-processing operations) based on a cine MRI and produce results that preserve the underlying anatomy of the heart.

As described herein, since the myocardium predicted by the motion estimation neural network system is tracked with corrected references that conform to the anatomy of the myocardium, the training of the motion estimation neural network system may be conducted in a minimally or weakly supervised manner (e.g., only the first image frame may be annotated). In addition, one or more refinement operations may be performed to prevent prediction errors such as accumulation errors from occurring during the tracking process. For instance, in the example(s) shown in FIG. 2 and/or FIG. 4, a warped image or mask $I'_n$ (e.g., obtained via $I'_n = \hat{F}_{1n} \otimes I_1$) that corresponds to a n-th image frame or mask $I_n$ may be compared to the n-th image frame/mask $I_n$ to derive an estimated flow $F^\delta_n$ between $I'_n$ and $I_n$. The motion between the first and the n-th image frame/mask may then be compensated in accordance with the following: $\hat{F}*_{1n} = \hat{F}_{1n} \oplus F^\delta_n$ (e.g., to warp the previously warped image/mask $I'_n$ again).

Further, the shape constraints or anatomy awareness described here may be infused into the training and/or operation of the motion estimation neural network system by determining and minimizing the difference between a segmentation mask predicted by the motion estimation neural network system and an anatomically realistic (e.g., anatomically correct) segmentation mask produced by the VAE in the latent space or based on a flow field (e.g., in addition to or in lieu of comparing the masks in the image space, as described herein). For example, an estimated mask produced by the motion estimation neural network system may be provided as input to the VAE encoder to obtain a first latent space vector at the bottle neck. A corresponding reference mask (e.g., an anatomically realistic mask) may also be provided to the VAE encoder to obtain a second latent space vector. The motion estimation neural network system may then be trained based on the first and second latent space vectors with an objective to minimize the difference between the two vectors (e.g., to make the latent space of the estimated mask approximate the latent space of the reference mask). In another example, a flow field may be determined between the estimated mask and the anatomically realistic reference mask, and a loss function may be derived based on the flow field to force the estimated mask to be similar to the reference mask. Various techniques may be used to enforce this condition. For instance, a L2 norm term of the flow field may be added to the loss function to directly force the flow field to be small based on a presumption that a small flow field between the estimated mask and the reference mask will make the estimated mask substantially similar to the reference mask.

By training the motion estimation neural network system with the anatomy-aware VAE described herein, shape or anatomy prior may be infused into the motion estimation neural network system so that, at an inference time (e.g., while performing a motion estimation task), the motion estimation neural network system may estimate an anatomically correct motion of the target anatomical structure, for example, without having to perform additional anatomy or shape correction operations during processing or post-processing. For instance, the VAE may be used to train the motion estimation neural network system (e.g., infusing shape/anatomy prior into the motion estimation parameters of the system) so that at the inference time, anatomy-preserving motion estimation may be performed directly without the VAE or other similar anatomy or shape correction components or systems (e.g., one or more post-processing steps may be omitted). The speed of the estimation may be improved as a result. The complexity of the motion estimation system may also be reduced.

The neural networks described herein (e.g., the motion estimation neural network system 200 and/or the anatomy-aware variational autoencoder) may be implemented using one or more processors, one or more storage devices, and/or other suitable accessory devices such as display devices, communication devices, input/output devices, etc. The storage devices may be configured to store instructions that, when executed by the one or more processors, cause the one or more processors to perform the functions described herein. The one or more processors may include a central processing unit (CPU), a graphics processing unit (GPU), a microcontroller, a reduced instruction set computer (RISC) processor, an application specific integrated circuit (ASIC), an application-specific instruction-set processor (ASIP), a physics processing unit (PPU), a digital signal processor (DSP), a field programmable gate array (FPGA), or a combination thereof. The one or more storage devices may include volatile or non-volatile memory such as semiconductor memory (e.g., electrically programmable read-only memory (EPROM), electrically erasable programmable read-only memory (EEPROM), etc.), flash memory, a mass storage device (e.g., a magnetic disk such as an internal hard disk, a removable disk, a magneto-optical disk, a CD-ROM or DVD-ROM disk, etc.).

In addition, although the examples are described herein with reference to various types of neural networks, various types of layers, and/or various tasks being performed by certain types of neural networks or layers, the references are made merely for illustration purposes and not meant to limit the scope of the disclosure. For example, in certain implementations, an encoder network and/or a decoder network may not include a fully connected layer and may still be able to perform the functions described herein. Further, even though a variational autoencoder is described in one or more of the examples, the implementation of the techniques disclosed herein is not limited to such a variational autoencoder. Other types of neural networks may also be used to realize the functionality described herein.

Each of the neural networks described herein may comprise multiple layers including an input layer, one or more convolutional layers, one or more non-linear activation layers, one or more pooling layers, one or more fully connected layers, and/or an output layer. Each of the layers may correspond to a plurality of filters (e.g., kernels) and each filter may be designed to detect (e.g., learn) a set of keypoints that collectively represent a respective feature or pattern. The filters may be associated with respective weights that, when applied to an input, produce an output indicating whether certain visual features or patterns have been detected. The weights associated with the filters may be learned by the neural networks through a training process that comprises inputting a large number of images from one or more training datasets to the neural networks, calculating differences or losses resulting from the weights currently assigned to the filters (e.g., based on an objective function such as mean squared error or L1 norm, a margin based loss function, etc.), and updating the weights assigned to the filters so as to minimize the differences or losses (e.g., based on stochastic gradient descent).

Figure 5:
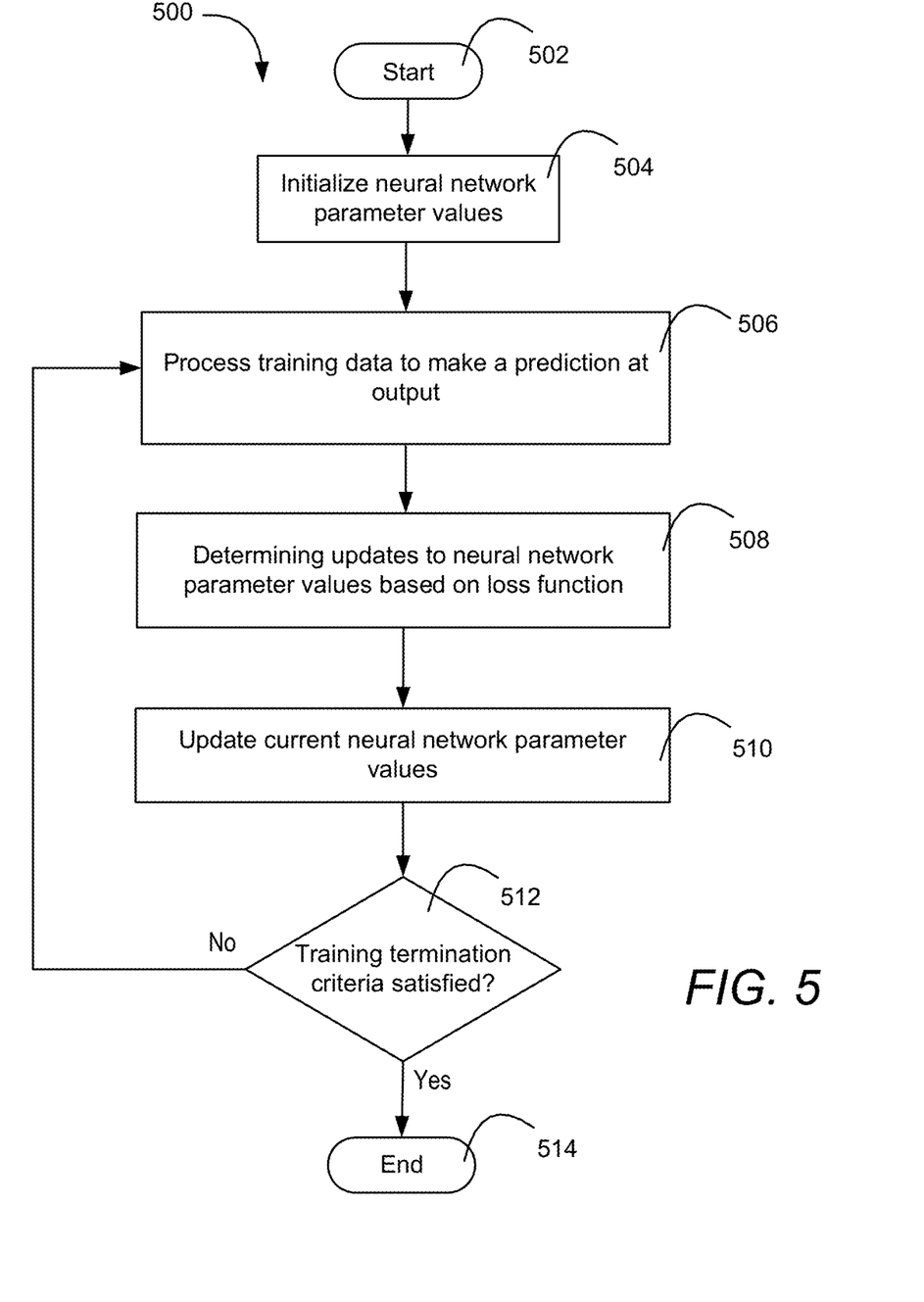
FIG. 5 is a flow diagram illustrating an example neural network training process.

FIG. 5 is a flow diagram of an example process 500 that may be implemented and executed during training of one or more of the neural networks described herein. The process 500 may be performed by a system of one or more computers (e.g., one or more processors) located in one or more locations. The process may start at 502 and, at 504, the system may initialize the operating parameters of the neural network (e.g., weights associated with one or more layers of the neural network). For example, the system may initialize the parameters based on samples from one or more probability distributions or parameter values of another neural network with a similar architecture. At 506, the system may process a training image and/or other training data such as a latent variable described herein using the current parameter values assigned to the layers. A prediction may be made as a result of the processing and at 508, the system may determine updates to the current parameter values, e.g., based on an objective or loss function and a gradient descent of the function. As described herein, the objective function may be designed to minimize the difference between the prediction and a ground truth. The objective function may be implemented using, for example, mean squared error, L1 norm, etc. At 510, the system may update the current values of the neural network parameters, for example, through a backpropagation process. At 512, the system may determine whether one or more training termination criteria are satisfied. For example, the system may determine that the training termination criteria are satisfied if the system has completed a pre-determined number of training iterations, or if the change in the value of the loss function between two training iterations falls below a predetermined threshold. If the determination at 512 is that the training termination criteria are not satisfied, the system may return to 506. If the determination at 512 is that the training termination criteria are satisfied, the system may end the training process 500 at 514.

For simplicity of explanation, the operation of the example system is depicted and described herein with a specific order. It should be appreciated, however, that these operations may occur in various orders, concurrently, and/or with other operations not presented or described herein. Furthermore, it should be noted that not all operations that the system is capable of performing are depicted and described herein, and not all illustrated operations are required to be performed by the system.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A neural network system comprising one or more processors and one or more storage devices, the one or more storage devices configured to store instructions that, when executed by the one or more processors, cause the one or more processors to:

receive a first medical image and a second medical image, wherein the first medical image comprises a first visual representation of an anatomical structure and the second medical image comprises a second visual representation of the anatomical structure;

extract a first plurality of features from the first medical image and a second plurality of features from the second medical image;

determine a first motion of the anatomical structure between the first medical image and the second medical image based on the first plurality of features and the second plurality of features respectively extracted from the first medical image and the second medical image; and generate a first flow field indicating the first motion;

wherein the neural network system is trained at least partially using a variational autoencoder (VAE) as a supervisor of the training, the VAE being pre-trained to generate a refined segmentation mask for the anatomical structure based on a shape prior of the anatomical structure, and wherein, during the training of the neural network system, the neural network system is configured to generate a coarse segmentation mask for the anatomical structure based on a first plurality of features extracted from a first training image or based on a second plurality of features extracted from a second training image, and adjust one or more operating parameters of the neural network system based on a first loss calculated from the coarse segmentation mask and the refined segmentation mask.

2. The neural network system of claim 1, wherein the VAE is pre-trained using a training dataset that represents a shape distribution of the anatomical structure, and, through the pre-training, the VAE learns to receive an input segmentation mask associated with the anatomical structure and generate a corrected version of the input segmentation mask that conforms with the shape distribution of the anatomical structure.

3. The neural network system of claim 2, wherein, during the training of the neural network system, the neural network system is further configured to:

estimate a baseline flow field based on two input training images of the anatomical structure;

generate a warped segmentation mask for the anatomical structure based on the baseline flow field;

obtain, from the VAE, a reconstructed segmentation mask for the anatomical structure that corresponds to the warped segmentation mask, wherein the reconstructed segmentation mask is generated by the VAE in accordance with the shape prior of the anatomical structure; and adjust the one or more operating parameters of the neural network system further based on a second loss calculated from the warped segmentation mask and the reconstructed segmentation mask.

4. The neural network system of claim 3, wherein the first loss and the second loss are assigned respective weights during the adjustment of the one or more operating parameters of the neural network system.

5. The neural network system of claim 4, wherein, during the training of the neural network system, the neural network system is further configured to obtain a warped image by warping a first one of the two input training images according to the baseline flow field, determine a third loss based on the warped image and a second one of the two input training images, and adjust the one or more operating parameters of the neural network system further based on the third loss.

6. The neural network system of claim 1, wherein the instructions, when executed by the one or more processors, further cause the one or more processors to determine a second motion of the anatomical structure based on the first plurality of features and the second plurality of features respectively extracted from the first medical image and the second medical image, and generate a second flow field indicating the second motion.

7. The neural network system of claim 6, wherein the instructions, when executed by the one or more processors, further cause the one or more processors to generate a first warped image based on the first flow field and the first medical image, and generate a second warped image based on the second flow field and the second medical image.

8. The neural network system of claim 7, wherein the instructions, when executed by the one or more processors, further cause the one or more processors to generate a third flow field that indicates a third motion of the anatomical structure from the first warped image to the second medical image, and generate a third warped image based on the third flow field and the first warped image.

9. The neural network system of claim 1, wherein the first plurality of features and the second plurality of features are respectively extracted from the first medical image and the second medical image using a neural network characterized by a symmetrical architecture.

10. The neural network system of claim 1, wherein the training of the neural network system is conducted using a training magnetic resonance imaging (MRI) video that comprises a plurality of image frames, and wherein only a first one of the image frames is annotated for the training.

11. A method for motion estimation implemented by a neural network system, the method comprising:
receiving a first medical image and a second medical image, wherein the first medical image comprises a first visual representation of an anatomical structure and the second medical image comprises a second visual representation of the anatomical structure;
extracting a first plurality of features from the first medical image and a second plurality of features from the second medical image;
determining a first motion of the anatomical structure between the first medical image and the second medical image based on the first plurality of features and the second plurality of features respectively extracted from the first medical image and the second medical image; and
generating a first flow field indicating the first motion;
wherein the neural network system is trained at least partially using a variational autoencoder (VAE) as a supervisor of the training, the VAE being pre-trained to generate a refined segmentation mask for the anatomical structure based on a shape prior of the anatomical structure, and wherein, during the training of the neural network system, the neural network system is configured to generate a coarse segmentation mask for the anatomical structure based on a first plurality of features extracted from a first training medical image or based on a second plurality of features extracted from a second training medical image, and adjust one or more operating parameters of the neural network system based on a first loss calculated from the coarse segmentation mask and the refined segmentation mask.

12. The method of claim 11, wherein the VAE is pre-trained using a training dataset that represents a shape distribution of the anatomical structure, and, through the pre-training, the VAE learns to receive an input segmentation mask associated with the anatomical structure and generate a corrected version of the input segmentation mask that conforms with the shape distribution of the anatomical structure.

13. The method of claim 12, wherein, during the training of the neural network system, the neural network system is further configured to:
estimate a baseline flow field based on two input training images of the anatomical structure;
generate a warped segmentation mask for the anatomical structure based on the baseline flow field;
obtain, from the VAE, a reconstructed segmentation mask for the anatomical structure that corresponds to the warped segmentation mask, wherein the reconstructed segmentation mask is generated by the VAE in accordance with the shape prior of the anatomical structure; and
adjust the one or more operating parameters of the neural network system further based on a second loss calculated from the warped segmentation mask and the reconstructed segmentation mask.

14. The method of claim 13, wherein the first loss and the second loss are assigned respective weights during the adjustment of the one or more operating parameters of the neural network system.

15. The method of claim 14, wherein, during the training of the neural network system, the neural network system is further configured to obtain a warped image by warping a first one of the two input training images according to the baseline flow field, determine a third loss based on the warped image and a second one of the two input training images, and adjust the one or more operating parameters of the neural network system further based on the third loss.

16. The method of claim 11, further comprising:
determining a second motion of the anatomical structure based on the first plurality of features and the second plurality of features respectively extracted from the first medical image and the second medical image; and
generating a second flow field that indicates the second motion.

17. The method of claim 16, further comprising generating a first warped image based on the first flow field and the first medical image and generating a second warped image based on the second flow field and the second medical image.

18. The method of claim 17, further comprising generating a third flow field that indicates a third motion of the anatomical structure from the first warped image to the second medical image and generating a third warped image based on the third flow field and the first warped image.

19. The method of claim 11, wherein the first plurality of features and the second plurality of features are respectively extracted from the first medical image and the second medical image using a neural network characterized by a symmetrical architecture.

20. The method of claim 11, wherein the training of the neural network system is conducted using a training magnetic resonance imaging (MRI) video that comprises a plurality of image frames, and wherein only a first one of the image frames is annotated for the training.

* * * * *